(12) United States Patent
Wang et al.

(10) Patent No.: US 11,311,742 B2
(45) Date of Patent: Apr. 26, 2022

(54) LASER THERAPEUTIC APPARATUS AND SPINAL CORD REPAIRING METHOD

(71) Applicant: XI'AN LASER TECH MEDICAL TECHNOLOGY COMPANY LIMITED, Xi'an (CN)

(72) Inventors: Yi Wang, Xi'An (CN); Tan Ding, Xi'An (CN)

(73) Assignee: XI'AN LASER TECH MEDICAL TECHNOLOGY CO., LTD., Xi'an (CN)

( * ) Notice: Subject to any disclaimer, the term of this patent is extended or adjusted under 35 U.S.C. 154(b) by 98 days.

(21) Appl. No.: 16/687,696

(22) Filed: Nov. 19, 2019

(65) Prior Publication Data
US 2020/0078601 A1   Mar. 12, 2020

Related U.S. Application Data

(63) Continuation of application No. PCT/CN2018/087922, filed on Jun. 13, 2018.

(30) Foreign Application Priority Data

May 23, 2017   (CN) .......................... 201710367037.1

(51) Int. Cl.
*A61N 5/06* (2006.01)
*A61N 5/067* (2006.01)

(52) U.S. Cl.
CPC ......... *A61N 5/0613* (2013.01); *A61N 5/0603* (2013.01); *A61B 2562/0247* (2013.01);
(Continued)

(58) Field of Classification Search
CPC ................ A61N 5/0613; A61N 5/0603; A61N 2005/0626; A61N 2005/063;
(Continued)

(56) References Cited

U.S. PATENT DOCUMENTS 5,721,635 A * 2/1998 Shigematsu ........ H01S 3/06754
359/337.3
8,328,857 B2 * 12/2012 Anders ................ A61N 5/0613
607/88
(Continued)

FOREIGN PATENT DOCUMENTS

WO   WO-2012098548 A1 *   7/2012   .......... A61N 5/0622

OTHER PUBLICATIONS

Ning Li and Gilberto Leung, Oligodendrocyte Precursor Cells in Spinal Cord Injury: A Review and Update, Mar. 12, 2015, Biomed Research International, vol. 2015 (Year: 2015).*
(Continued)

*Primary Examiner* — Brian T Gedeon
*Assistant Examiner* — Joshua Andrew Schum-Houck
(74) *Attorney, Agent, or Firm* — Hemisphere Law, PLLC; Zhigang Ma

(57) ABSTRACT

A laser therapeutic apparatus includes a laser and a therapeutic optical fiber. The therapeutic optical fiber is configured for being implanted into a body of a patient during surgery to perform a repair treatment on a spinal cord site to-be-treated by irradiation and then being removed from the body of the patient after the surgery. The therapeutic optical fiber includes N number of laser fibers, N−1 number of optical fiber connection components, an optical fiber guiding structure, and an optical fiber controller; the N number of laser fibers are coupled with one another by the N−1 number of optical fiber connection components to form a cascaded optical fiber structure, an end of the cascaded optical fiber structure is coupled to the optical fiber guiding structure, and another end of the cascaded optical fiber structure is coupled to the optical fiber controller.

17 Claims, 4 Drawing Sheets

(52) U.S. Cl.
CPC ........ *A61N 5/067* (2021.08); *A61N 2005/063* (2013.01); *A61N 2005/0626* (2013.01)

(58) Field of Classification Search
CPC ...... A61N 2005/067; A61N 2005/0632; A61N 5/0601; A61N 5/0622; A61N 2005/0664; A61B 2562/0247; A61B 2018/2244; A61B 2018/2211
See application file for complete search history.

(56) References Cited

U.S. PATENT DOCUMENTS

| | | | |
|---|---|---|---|
| 9,180,308 B1* | 11/2015 | Frost | A61N 5/0618 |
| 2002/0164130 A1* | 11/2002 | Elkins, II | G02B 6/3887 |
| | | | 385/87 |
| 2004/0201000 A1* | 10/2004 | Norwood | C08L 85/02 |
| | | | 252/582 |
| 2006/0013550 A1* | 1/2006 | Ingman | G02B 6/02333 |
| | | | 385/128 |
| 2006/0030753 A1* | 2/2006 | Boutillette | A61B 1/0057 |
| | | | 600/146 |
| 2009/0240242 A1* | 9/2009 | Neuberger | A61B 18/24 |
| | | | 606/7 |
| 2009/0259216 A1* | 10/2009 | Drew | A61N 1/3706 |
| | | | 604/891.1 |
| 2009/0324175 A1* | 12/2009 | Everett | G02B 6/383 |
| | | | 385/72 |
| 2011/0122646 A1* | 5/2011 | Bickham | G02B 6/02347 |
| | | | 362/554 |
| 2012/0020618 A1* | 1/2012 | Erdman | G02B 6/3851 |
| | | | 385/33 |
| 2012/0253261 A1* | 10/2012 | Poletto | A61N 5/0601 |
| | | | 604/20 |
| 2013/0073011 A1* | 3/2013 | Anders | A61N 5/0613 |
| | | | 607/88 |
| 2013/0074303 A1* | 3/2013 | Durrant | G02B 6/2558 |
| | | | 29/402.14 |
| 2014/0188197 A1* | 7/2014 | Schenker | A61N 5/0622 |
| | | | 607/89 |
| 2015/0093573 A1* | 4/2015 | Sevier | H01B 13/0023 |
| | | | 428/375 |
| 2015/0360050 A1* | 12/2015 | Kaplitt | A61N 5/0622 |
| | | | 607/88 |
| 2016/0030765 A1* | 2/2016 | Towne | A61N 5/0622 |
| | | | 607/88 |
| 2016/0365721 A1* | 12/2016 | Soma | H03K 19/017509 |
| 2017/0003459 A1* | 1/2017 | Takeuchi | G02B 6/3821 |
| 2017/0087055 A1* | 3/2017 | Tseng | A61H 39/086 |

OTHER PUBLICATIONS

Ivana Novotna Grulova, Ivo Vanicky, IT delivery of ChABC modulates NG2 and promotes GAP-43 axonal regrowth after spinal cord injury, Jun. 2011, Cellular and Molecular Neurobiology (Year: 2011).*

* cited by examiner

LASER THERAPEUTIC APPARATUS AND SPINAL CORD REPAIRING METHOD

TECHNICAL FIELD

The disclosure relates to the technical field of laser treatment/therapy, and particularly relates to a laser therapeutic apparatus and a spinal cord repairing method.

BACKGROUND

Current production lifestyles, sports, and various types of traffic accidents are accompanied by more or less, or light or severe nerve damage, and existing clinical treatment strategies are decompression, fixation, necessary braking, and drug-assisted treatment. Spinal cord injury is the most serious type of nerve injury. Spinal cord injuries (SCI) should be considered when there is a sensation, movement, reflex or sphincter dysfunction below the plane of the injured segment after spinal trauma.

For the treatment of spinal cord injury, the current clinically mainly through neurosurgery and orthopedic surgery to relieve the compression of the spinal cord. Emphasis is placed on the use of high-dose hormonal shock therapy within 8 hours of injury to increase the spinal cord's ability to resist injury. In recent years, some new treatments have emerged, but the effects are not obvious.

After acute and chronic spinal cord injury, a series of pathophysiological changes occur in the spinal cord, which will produce a series of adverse events at different time segments. The chronological order generally includes: hemorrhage, edema, autoinflammatory reaction, microcirculatory disorder, calcium influx, free radical formation, secondary ischemia and hypoxia, neurodegenerative, neuropathic pain, and glial scar formation. The above adverse events together constitute a barrier that affects spinal nerve regeneration and rehabilitation. However, the existing treatment methods cannot directly treat the pathological changes of the above spinal cord injury effectively.

SUMMARY

In order to solve the above problems existing in the prior art, the disclosure provides a laser therapeutic apparatus and a spinal cord repairing method.

An embodiment of the disclosure provides a laser therapeutic apparatus, including a laser; and a therapeutic optical fiber, coupled to the laser and driven by the laser to emit light; wherein the therapeutic optical fiber is configured for being implanted into a body of a patient during surgery to perform a repair treatment on a spinal cord site to-be-treated by irradiation and then being removed from the body of the patient after the surgery.

The therapeutic optical fiber includes N number of laser fibers each with a predetermined length, N−1 number of optical fiber connection components, an optical fiber guiding structure, and an optical fiber controller; the N number of laser fibers are coupled with one another by the N−1 number of optical fiber connection components to form a cascaded optical fiber structure, an end of the cascaded optical fiber structure is coupled to the optical fiber guiding structure, and another end of the cascaded optical fiber structure is coupled to the optical fiber controller, and N is a positive integer; each of the optical fiber connection components is provided with a pressure sensor, and the pressure sensor is coupled to the optical fiber controller, the pressure sensor is configured to detect pressure data of the optical fiber connection component, and the optical fiber controller is configured to determine a coupling state of the laser fiber based on the pressure data.

In a specific embodiment, the therapeutic optical fiber is a 360° circumferentially illuminated full-body luminous optical fiber.

In a specific embodiment, the laser is a semiconductor laser having a laser wavelength of 770 nm to 830 nm.

In a specific embodiment, the optical fiber connection component (2) includes a first collimator (21) and a second collimator (22); the first collimator (21) and the second collimator (22) are respectively disposed ends of two of the N number of laser fibers (1), and the first collimator (21) and the second collimator (22) are attached to each other such that the two of the N number of laser fibers (1) are axially coincided with each other.

In a specific embodiment, the optical fiber connection component (2) further includes a silicone rubber sleeve (23), the silicone rubber sleeve (23) is sleeved on the first collimator (21) and the second collimator (22), the pressure sensor (6) is disposed between the silicone rubber sleeve (23) and the first collimator (21) and/or the second collimator (22).

In a specific embodiment, a lateral limiting ring is further disposed at an interface between the laser fiber and corresponding one of the first and second collimators.

In a specific embodiment, a distance from the lateral limiting ring to the corresponding one of the first and second collimators is in a range from 2 mm to 8 mm.

In a specific embodiment, a ratio of a diameter of the lateral limiting ring to a diameter of the laser fiber is in a range from 4:3 to 3:2.

In a specific embodiment, the lateral limiting ring is coated with a tetrafluoroethylene coating.

In an embodiment of the disclosure, the laser includes a power source, a processor, a laser output circuit, an input control circuit, and a laser light source;

the processor is electrically coupled to the input control circuit and the laser output circuit and configured for controlling the laser output circuit according to a control instruction inputted from the input control circuit;

the laser output circuit is electrically coupled to the laser light source and configured for controlling an irradiation intensity and an irradiation duration of the laser light source;

the power source is electrically coupled to the laser output circuit and configured for providing a driving current to the laser output circuit.

In an embodiment of the disclosure, the laser output circuit includes a power control circuit and a laser driving circuit;

the power control circuit is electrically coupled to the processor, the power source and the laser driving circuit individually, and configured for converting a rated voltage outputted from the power source into a required constant driving current according to the control instruction inputted to the processor, and further configured for outputting the driving current to the laser driving circuit to drive the laser driving circuit to operate;

the laser driving circuit is electrically coupled to the laser light source and configured for controlling the irradiation intensity and the irradiation duration of the laser light source.

In an embodiment of the disclosure, the laser further includes a feedback protection circuit; the feedback protection circuit includes an overcurrent protection circuit, a power feedback circuit and a temperature feedback circuit;

the overcurrent protection circuit is electrically coupled to the power control circuit and the processor, and configured for detecting a current of the power control circuit and transmitting a current information to the processor;

the power feedback circuit and the temperature feedback circuit each are electrically coupled to both the laser driving circuit and the processor, and configured for detecting a power and a temperature of the laser driving circuit and transmitting a power information and a temperature information to the processor.

Another embodiment of the disclosure provides a spinal cord repairing method for performing spinal cord repair by a laser therapeutic apparatus, wherein the method includes:

determining laser irradiation parameters of the laser therapeutic apparatus according to spinal nerve function and degree of injury of a patient;

implanting the therapeutic optical fiber of the laser therapeutic apparatus into a spinal cord site to-be-treated in a body of the patient during a surgery operation;

after the surgery operation, controlling the laser therapeutic apparatus to irradiate the spinal cord site to-be-treated for repair according to the determined laser irradiation parameters, wherein the spinal cord site to-be-treated is irradiated in a manner of first continuous irradiation and then pulsed irradiation, or in a manner of first pulsed irradiation and then continuous irradiation; and removing the therapeutic optical fiber after completion of the repair.

In an embodiment of the disclosure, the laser irradiation parameters include working mode of laser irradiation, laser wavelength, laser irradiation intensity, and laser irradiation duration.

In an embodiment of the disclosure, the method further includes:

adjusting the laser irradiation parameters according to observed changes in TNF-α factor, IL-6 factor, IL-10 factor, NG2 protein and GAP43 protein of the patient.

In the embodiment of the disclosure, by using an implantable therapeutic fiber, the laser controls its luminescence according to the characteristics of the spinal cord injury. Using the biological properties of low-intensity laser photochemistry, thermal effects, light pressure and bio stimulating effects, cells and molecules such as mitochondria are irradiated to achieve damage repair to the spinal cord. It is possible to directly change the pathology of spinal cord injury and provide the effect of spinal cord repair treatment.

DETAILED DESCRIPTION OF EMBODIMENTS

Figure 1:
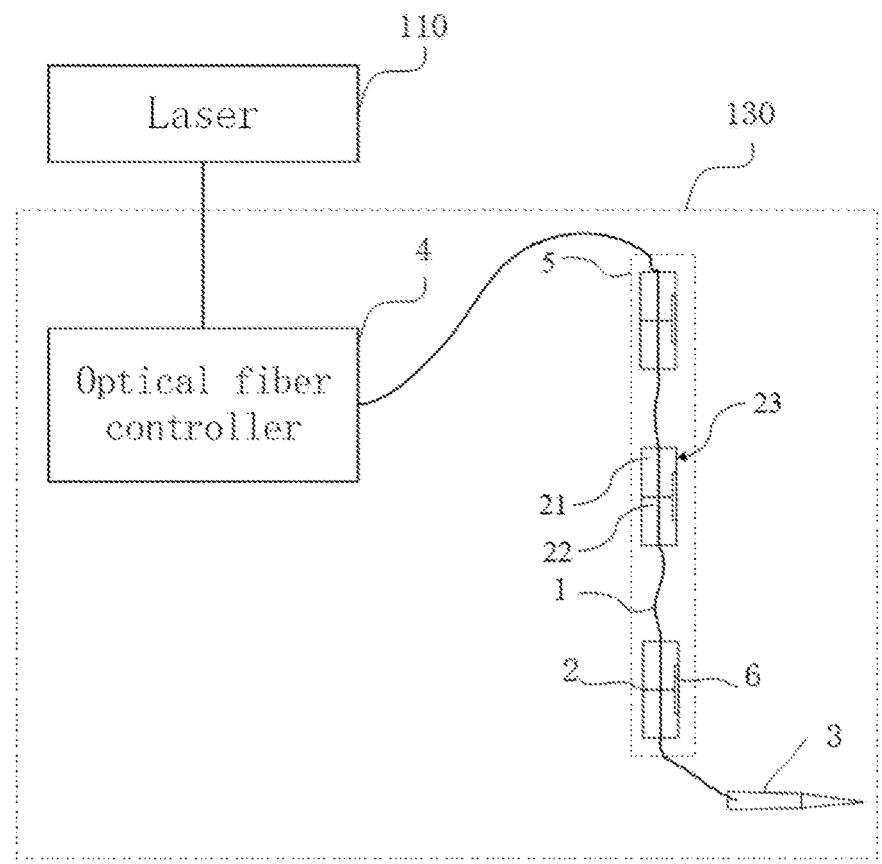
FIG. 1 is a schematic structural diagram of a laser therapeutic apparatus according to an embodiment of the disclosure.

The disclosure will be further described in detail below with reference to specific embodiments, but embodiments of the disclosure are not limited thereto.

A spinal cord repairing method of the disclosure and a laser therapeutic apparatus as invented belong to one of low-intensity laser therapies. A laser therapeutic apparatus was first used in wound healing and pain relief, and its medical use has been widely expanded to treat a variety of diseases, including stroke, myocardial infarction, degenerative or traumatic brain disease, spinal cord injury, peripheral nerve regeneration and other fields. However, there is currently no implantable application for spinal cord repair.

The disclosure mainly utilizes its biological stimulation effect to produce a biological stimulation similar to ultrasonic or acupuncture. The low-intensity laser therapeutic apparatus of the disclosure mainly aims at adverse events such as hemorrhage, edema, autoinflammatory reaction, microcirculatory disorder, calcium influx, free radical formation, secondary ischemia and hypoxia, neurodemyelination, neuropathic pain and glial scar formation in spinal cord injury, and fully evaluates the spinal nerve function and degree of injury in the patient before surgery, and formulates an irradiation treatment plan/scheme. During the surgery, a specialized therapeutic optical fiber was implanted. After the surgery, an effective irradiation site is used to go against many adverse events of spinal nerve injury by adjusting an irradiation time, an irradiation energy, an irradiation manner and an irradiation wavelength of laser, so that each adverse event is relieved to different extents than untreated groups.

Specifically, after basic researches, it was found that the low-intensity laser has the following mechanism of action on the injury of neurospinal cord:

Mechanism of action 1: Reduction of immune inflammatory response. In several experiments, it was found that the expression of TNF-α was decreased after low-intensity laser irradiation, and the difference was statistically significant at 6 h, 12 h and 1 d. These times are in the acute phase of spinal cord injury, which is the period with the highest expression of pro-inflammatory factor TNF-α. Similarly, IL-6 expression was also reduced after low-intensity laser irradiation, and the difference was statistically significant at 6 h, 12 h, and 5 d. In addition, it was found that IL-6 had a second peak of expression at the 5th day for a control group, while the peak was disappeared for the low-intensity laser irradiation group.

Mechanism of action 2: Increasement of neuroprotection. Unlike TNF-α and IL-6, IL-10 is an anti-inflammatory factor. In recent years, it has been found to be a neuroprotective factor with direct neuroprotective effects. Moreover, it was found that the expression rate and amount of IL-10 were significantly increased after low-intensity laser irradiation, which was favorable for inhibiting secondary inflammatory reaction.

Mechanism of action 3: Reduction for formation of glial scars in the spinal cord injury area and promotion for axonal regeneration. After spinal cord injury, the control group had a large amount of NG2 expression at the edge of the injured area, and the expression of GAP-43 was weak, while the expression of NG2 in the injured area of the low-intensity laser irradiation group was significantly weakened, and the expression of GAP-43 was enhanced. The expression of NG2 protein in the injury control group reached a peak on the 7th day after injury, and then the expression gradually decreased, which is consistent with the results reported in the literature. The expression of NG2 was significantly reduced after low-intensity laser irradiation, and the difference was statistically significant at 7 d, 14 d and 21 d after injury. The expression of GAP-43 protein was significantly increased after low-intensity laser irradiation. Detection of NG2 and GAP43 at gene levels also showed results in consistent with that at protein levels.

Mechanism of action 4: Reduction for hematoma edema of the injured spinal cord. In the early stage of spinal cord injury, the rats in the injured control group had diffuse hyperemia and edema on the dorsal side of the spinal cord, and the adhesion to the surrounding tissues was severe; in the late stage of spinal cord injury, the spinal cord was atrophied and scarred, and scar formation was observed. By contrast, in the low-intensity laser irradiation group, the degree of hemorrhage, edema and scar formation were mild.

Hereinafter, the disclosure will be described in detail from two aspects of a laser therapeutic apparatus and a spinal cord repairing method.

Embodiment 1

Please refer to FIG. 1. FIG. 1 is a schematic structural diagram of a laser therapeutic apparatus according to an embodiment of the disclosure. The laser therapeutic apparatus 10 includes a laser 110 and a therapeutic optical fiber 130 coupled to the laser 110 and driven to emit light by the laser 110. The therapeutic optical fiber 130 is implanted in a patient during a surgery to perform an irradiation repair treatment on a spinal cord portion to-be-treated and then is removed from the patient after the surgery.

The therapeutic optical fiber 130 includes N number of laser fibers 1 each with a predetermined length, N−1 number of optical fiber connection components 2, an optical fiber guiding structure 3, and an optical fiber controller 4. The N number of laser fibers 2 are coupled with one another by the N−1 number of optical fiber connection components 1 to form a cascaded optical fiber structure 5. An end of the cascaded optical fiber structure 5 is coupled to the optical fiber guiding structure 3, and another end of the cascaded optical fiber structure 5 is coupled to the optical fiber controller 4, where N is a positive integer e.g., no less than 2. Each of the optical fiber connection components 2 is provided with a pressure sensor 6, and the pressure sensor 6 is coupled to the optical fiber controller 4. The pressure sensor 6 is configured (i.e., structured and arranged) to detect pressure data of the optical fiber connection component 2, and the optical fiber controller 4 is configured to determine a coupling state of the laser fiber based on the pressure data. The fiber controller 4 can be a control chip such as an MCU, as long as it is capable of realizing data receiving, data sending, data displaying and alarming.

The optical fiber guiding structure 3 may be made of silica gel or other medical materials such as metal, or a combination of the above medical materials. It can realize that during the surgery operation, it is easy for surgical instruments such as surgical forceps to brace, drag (the optical fiber guiding structure has no fiber inside) or guide (a color of the optical fiber guiding structure is different from that of the other parts of the optical fiber, that is, the color of non-optical fiber guiding structure portion) the entire optical fiber, and even skin penetration operation (can be used as a guiding needle). If it is a metal guiding needle, it can be cut off after the optical fiber enters the surgical field. In a specific embodiment, the guiding needle can be a puncture dialysis needle for an arteriovenous dialysis catheter or an arteriovenous puncture needle.

In one scenario, the entire optical fiber therapeutic system includes a therapeutic apparatus and a therapeutic optical fiber, and the therapeutic apparatus includes an instrument and an internal optical fiber. Since the therapeutic optical fiber is directly connected to the therapeutic apparatus, which results in the therapeutic optical fiber is too long, and the interface is easy to damage resulting from frequent plugging and unplugging, the therapeutic apparatus of the embodiment of the disclosure is equipped with an internal optical fiber. The internal optical fiber is responsible for the connection of the therapeutic apparatus to the therapeutic optical fiber, but it is part of the therapeutic apparatus. The therapeutic optical fiber of the embodiment extends into the human body along a pre-designed path, and in the process, the pressure sensors collect pressure data in real time (e.g., every 30-100 ms) and transmit the pressure data to the optical fiber controller 4, and the operator judges the working condition of each optical fiber based on the pressure data. If the pressure of a certain optical fiber is too large, checks whether the optical fiber encounters an excessively large twisting stress and adjusts the path in time to prevent the optical fiber from being damaged or the optical fiber from damaging the human tissue.

Taking N=4 as an example, the therapeutic optical fiber includes four laser fibers, three optical fiber connection components, one optical fiber guiding structure, and one optical fiber controller. According to the connection relationship, the connection order/path is the optical fiber controller, one laser fiber, one optical fiber connection component, one laser fiber, one optical fiber connection component, one laser fiber, one optical fiber connection component, one laser fiber, and the optical fiber guiding structure. The laser signal is also transmitted through this path. Under normal circumstances, one end of the optical fiber guiding structure extends into the human body tissue, and the optical fiber controller is left outside the human body tissue to receive and feedback pressure data. Specifically, the number/quantity of the laser fibers and the number of corresponding optical fiber connection components are determined according to specific conditions. When the laser is transmitted in the optical fibers, there is transmission loss, and the longer the transmission path, the greater the loss is. The existing therapeutic optical fiber is generally of a fixed length. For different application scenarios, actually required lengths for the therapeutic optical fibers may be different, and thus the existing therapeutic optical fiber cannot be properly adapted. Therefore, the embodiment of the disclosure can adjust the length of the therapeutic optical fiber for a specific scenario, so as to facilitate modular management and improve the usage effect. In addition, due to some scenarios, after one treatment is completed, the optical fiber still needs to stay inside the human tissue for the next treatment, and therefore, if a complete optical fiber is used, the disassembly thereof is troublesome, and the modular optical fibers can independently control the optical fiber according to the patient's conditions.

During normal treatment and normal implantation in the body, the optical fiber is in a relatively static state in the human tissue, and the pressure generated by the surrounding tissue on the optical fiber is generally relatively constant. If the pressure data collected during this process fluctuates greatly. or the pressure being increased or decreased is more obvious, it can help determine whether the optical fiber is displaced in the human tissue and thereby avoid medical accidents.

By serially connecting a plurality of laser fibers, the activity of the optical fiber in the human tissue can be effectively enhanced, and the problem in the prior art that it is difficult to control after bending due to a long working distance is solved. Moreover, by setting a pressure sensor at the interface position of each segment of the optical fiber, the controllability of the optical fiber in the human body is further enhanced, the problem of damage of the optical fiber is prevented, and the treatment risk is reduced consequently.

The laser 110 may be a high-power fiber-coupled laser having a power of, for example about 1 watt, and a laser wavelength of 770 nm to 830 nm.

Preferably, the laser 110 has a laser wavelength of 770 nm to 830 nm. The advantage is that the laser wavelength can increase the level of beta-endorphin, promote the excretion of glucocorticoids in the urine, increase the threshold of pain under pressure through a complex electrolyte nerve fiber blocking mechanism, reduce the release of histamine and acetylcholine, reduce the synthesis of bradykinin, increase the production of adenosine triphosphate (ATP), improve local microcirculation, and promote lymphatic flow to thereby reduce edema. The final result is to promote nerve repair and reduce nerve pain.

Preferably, the therapeutic optical fiber is a 360° circumferentially illuminated full-body luminous optical fiber. The full-body luminous optical fiber may be divided into a solid core full-body luminous optical fiber or a liquid core full-body luminous optical fiber. Since the full-body luminous optical fiber exhibits an exponential decrease in the luminous intensity of the whole body as its length increases, the disclosure preferably employs a 360° circumferentially illuminated structure with a wavelength in the range of 770 nm to 830 nm, so as to achieve optimum luminescent properties.

Figure 2:
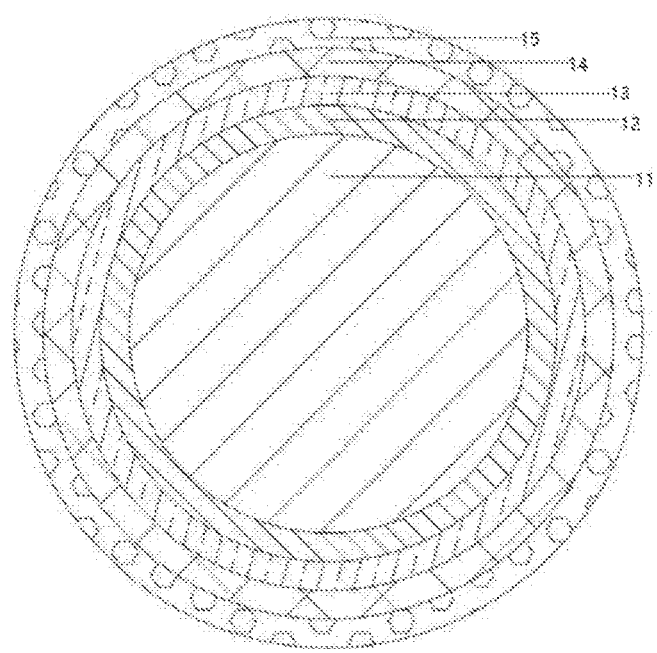
FIG. 2 is a schematic structural diagram of a therapeutic optical fiber according to an embodiment of the disclosure.

Specifically, please refer to FIG. 2. FIG. 2 is a schematic structural diagram of a laser fiber according to an embodiment of the disclosure.

The laser fiber 1 may be a medical quartz fiber, including quartz glass, silicone resin or hard polyfluoride. The laser fiber 1 includes a core 11, a cladding layer 12, a metal coating layer 13, an elastic coating layer 14, and a hydrophilic layer 15 in this order from the inside to the outside.

The core 11 of the embodiment may be a dispersion fiber, which is also called as a columnar emission fiber, and is a dispersion fiber for omnidirectional uniform illumination, that is, a 360° circumferentially illuminated full-body luminous optical fiber. The 360° circumferentially illuminated full-body luminous optical fiber includes a diffusing head and a light guiding fiber, and has high light transmission efficiency, can withstand high laser power density, has a small diffusing head and a smooth surface, and is suitable for implanting in a wound. It has a diameter of 1 mm to 5 mm, an usage temperature range of 0 to 60 degrees, and a spectral range of 200 nm to 2000 nm. The metal coating layer 13 can ensure the strength of the core 11, the elastic coating layer 14 can ensure the flexibility of the core 11, the hydrophilic layer 15 has good biocompatibility, and the safety of the optical fiber in the human tissue is improved. The elastic coating layer 14 exemplarily includes silicone rubber, a high strength polyester material, or the like.

In a specific embodiment, at least one fixing member is further fixed on the laser fiber, and the fixing member is fixedly disposed on the optical fiber extending outside the body for the surgical line to pass through. In general, since a treatment cycle varies from a few days to tens of days, the laser fiber is generally taken out of the body at the end of the treatment. During this period, the patient needs to carry the laser fiber during the non-treatment period, and if it is not fixed, it may cause the optical fiber to be displaced, causing serious medical accidents. Therefore, it is necessary to fix the laser fiber in the patient's body and the part extending outside the body. Generally, it only needs to fix the laser fiber in vitro, and the portion thereof inside the body is fixed consequently. After the surgical treatment cycle is completely finished, a fixing line of the external part of the laser fiber is directly removed, and then the optical fiber in the body is removed. The existing fixation method cannot fix the fiber well, the embodiment of the disclosure passes a surgical thread through the fixing member and fixes the surgical line to achieve an overall fixation, and in a preferred embodiment, the surgical line passes through the fixing member and then sutures to the skin adjacent to a position which the fiber penetrates through so as to enhance the fixation effect.

Optionally, the laser therapeutic apparatus may further include a heat dissipation system, and the heat generated during a working process of the laser 110 is dissipated in time by the air-cooling heat dissipation device to ensure that the laser 110 works within a safe temperature range, and the long-term reliability of the laser 110 is achieved.

In the illustrated embodiment of the disclosure, an implantable therapeutic optical fiber is used, and the laser controls its luminescence according to the characteristics of the spinal cord injury. Using the biological characteristics of photochemical, thermal effect, light pressure and bio stimulatory effects of low-intensity lasers, cells and molecules such as mitochondria are irradiated to achieve damage repair for the spinal cord, as well as direct change aiming at pathology of spinal cord injury, and thereby provide the effect of spinal cord repair treatment.

Embodiment 2

Figure 3:
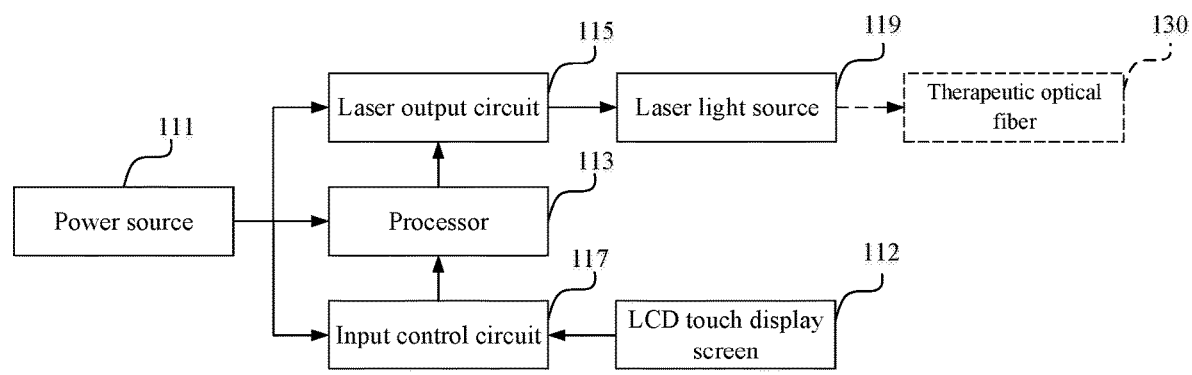
FIG. 3 is a schematic structural diagram of circuits of a laser according to an embodiment of the disclosure.

Referring to FIG. 3, FIG. 3 is a schematic structural diagram of circuits of a laser according to an embodiment of the disclosure. This embodiment focuses on the circuit structure of the laser on the basis of the above embodiment.

The laser 110 can include a power source 111, a processor 113, a laser output circuit 115, an input control circuit 117, and a laser light source 119. The processor 113 is electrically coupled to the input control circuit 117 and the laser output circuit 115, and configured to control, according to a control instruction/command inputted by the input control circuit 117, the laser output circuit 115 to output a laser with set working mode, set wavelength, set time and set energy. The laser output circuit 115 is electrically coupled to the laser light source 119 and configured for controlling illumination intensity and illumination duration of the laser light source 119. The power source 111 is electrically coupled to the laser output circuit 115 and configured for supplying a driving current to the laser output circuit 115.

Further, the laser 110 further includes an LCD touch display screen 112. The LCD touch display screen 112 is electrically coupled to the input control circuit 117 and configured for receiving the control command of the user and displaying current working state of the laser 110.

The power source 111 can be a 220V AC power source. The processor 113 can be a device having a processing function such as a microcontroller MCU, a single chip computer, or a programmable logic controller FPGA.

Figure 4:
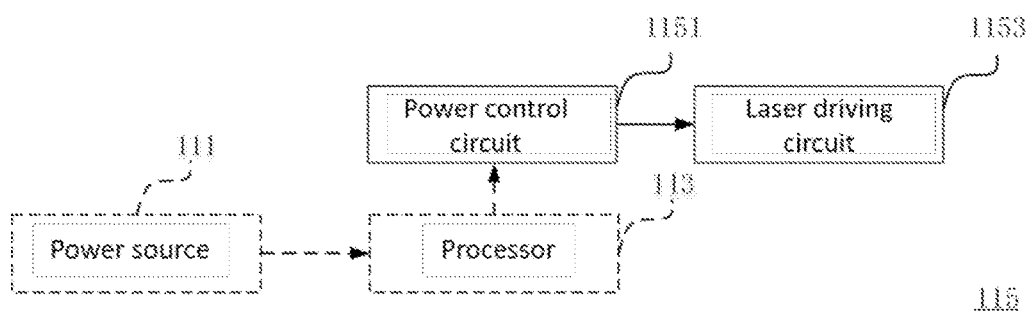
FIG. 4 is a schematic structural diagram of a laser output circuit according to an embodiment of the disclosure.

Preferably, please refer to FIG. 4. FIG. 4 is a schematic structural diagram of the laser output circuit according to an embodiment of the disclosure. The laser output circuit 115 includes a power control circuit 1151 and a laser driving circuit 1153. The power control circuit 1151 is electrically coupled to the processor 113, the power source 111 and the laser driving circuit 1153 individually, and configured for converting a rated voltage outputted from the power source 111 into a required constant driving current according to the control instruction of the processor 113, and outputting the driving current to the laser driving circuit 1153 to drive the laser driving circuit 1153 to operate. The laser driving circuit 1153 is electrically coupled to the laser light source 119 and configured for controlling the illumination intensity and the illumination duration of the laser light source 119.

Figure 5:
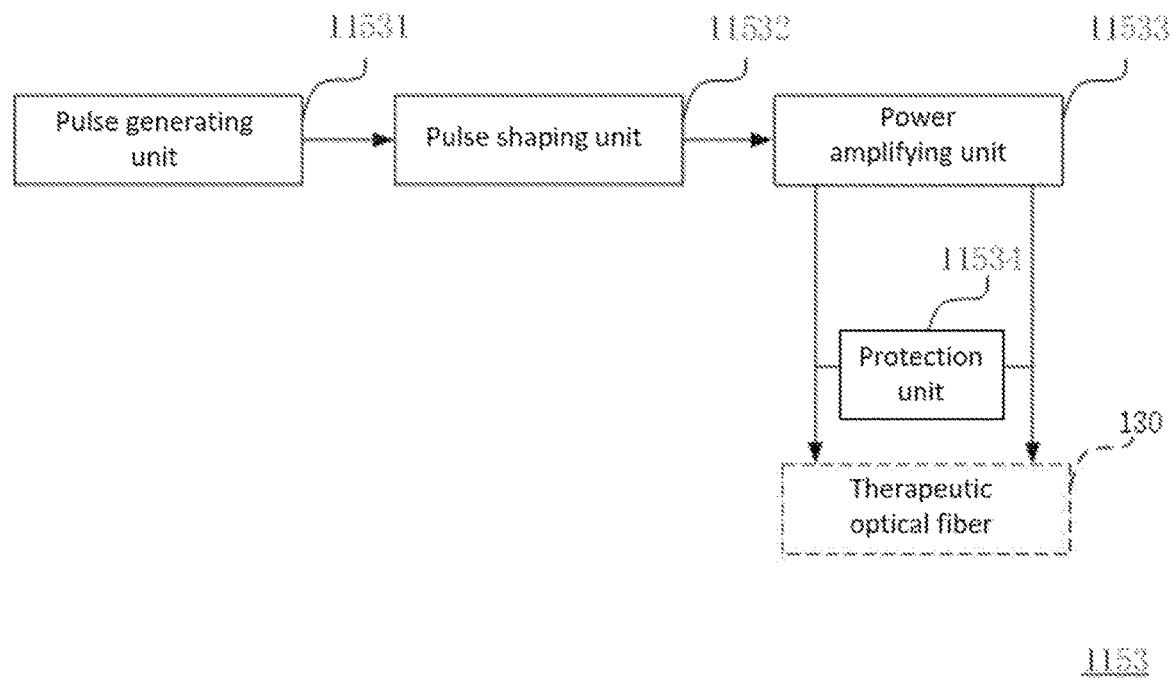
FIG. 5 is a schematic structural diagram of a laser driving circuit according to an embodiment of the disclosure.

Specifically, please refer to FIG. 5. FIG. 5 is a schematic structural diagram of the laser driving circuit according to an embodiment of the disclosure. The laser driving circuit 1153 includes a pulse generating unit 11531, a pulse shaping unit 11532, a power amplifying unit 11533, and a protection unit 11534. The pulse generating unit 11531, the pulse shaping unit 11532, the power amplifying unit 11533 and the therapeutic optical fiber 130 are electrically connected in sequence in that order. The protection unit 11534 is connected between connection nodes of the power amplifying unit 11533 with the therapeutic optical fiber 130.

In addition, the laser therapeutic apparatus may further include a laser protection system for real-time monitoring and early warning of temperature, current, and optical power, timing, feedbacking, and turning off the laser 110 in an abnormal state, so as to ensure the safety of the laser 110 and the patient.

Figure 6:
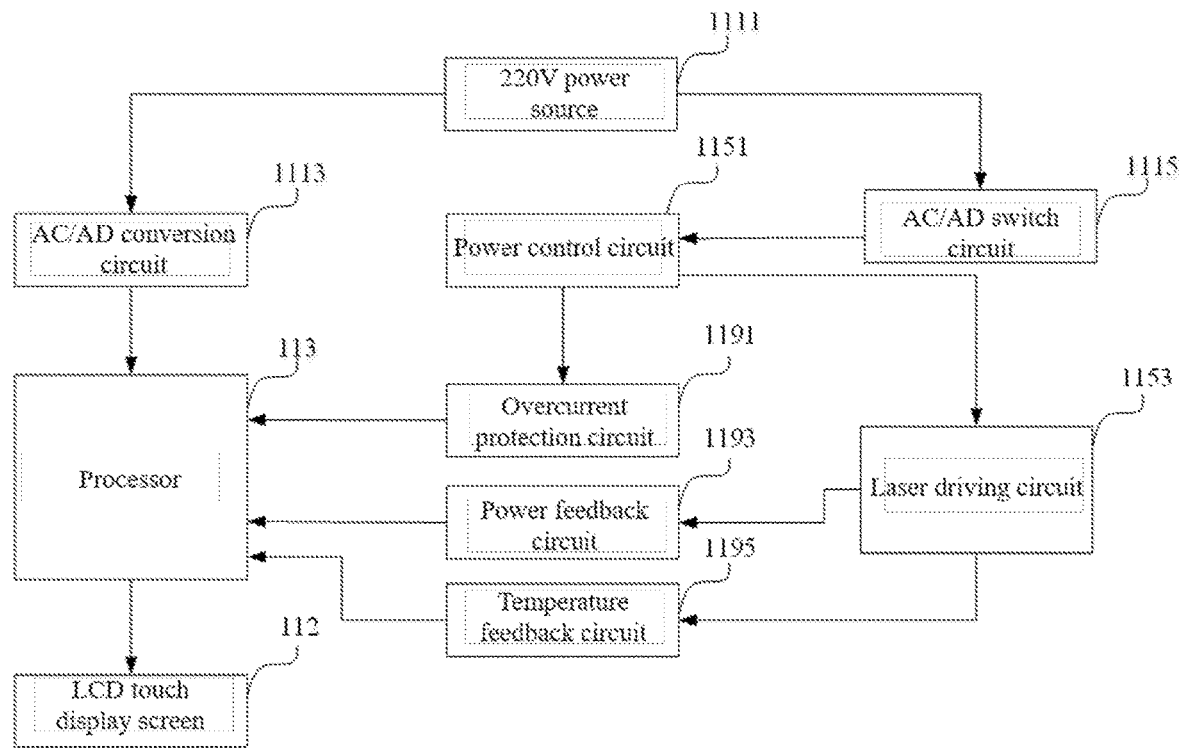
FIG. 6 is a schematic structural diagram of circuits of a laser according to another embodiment of the disclosure.

Specifically, please refer to FIG. 6. FIG. 6 is a schematic structural diagram of circuits of the laser according to another embodiment of the disclosure. The laser 110 further includes a feedback protection circuit 119. The feedback protection circuit 119 includes an overcurrent protection circuit 1191, a power feedback circuit 1193 and a temperature feedback circuit 1195. The overcurrent protection circuit 1191 is electrically coupled to the power control circuit 1151 and the processor 113, and configured for detecting a current of the power control circuit 1151 and transmitting current information to the processor 113. The power feedback circuit 1193 and the temperature feedback circuit 1195 each are electrically coupled to both of the laser driving circuit 1153 and the processor 113, and configured for detecting power and temperature of the laser driving circuit 1153 and transmitting power and temperature information to the processor 113.

The power source 111 may include a 220V power source 1111, an AC/AD conversion circuit 1113, and an AC/AD switch circuit 1115.

Embodiment 3

Figure 7:
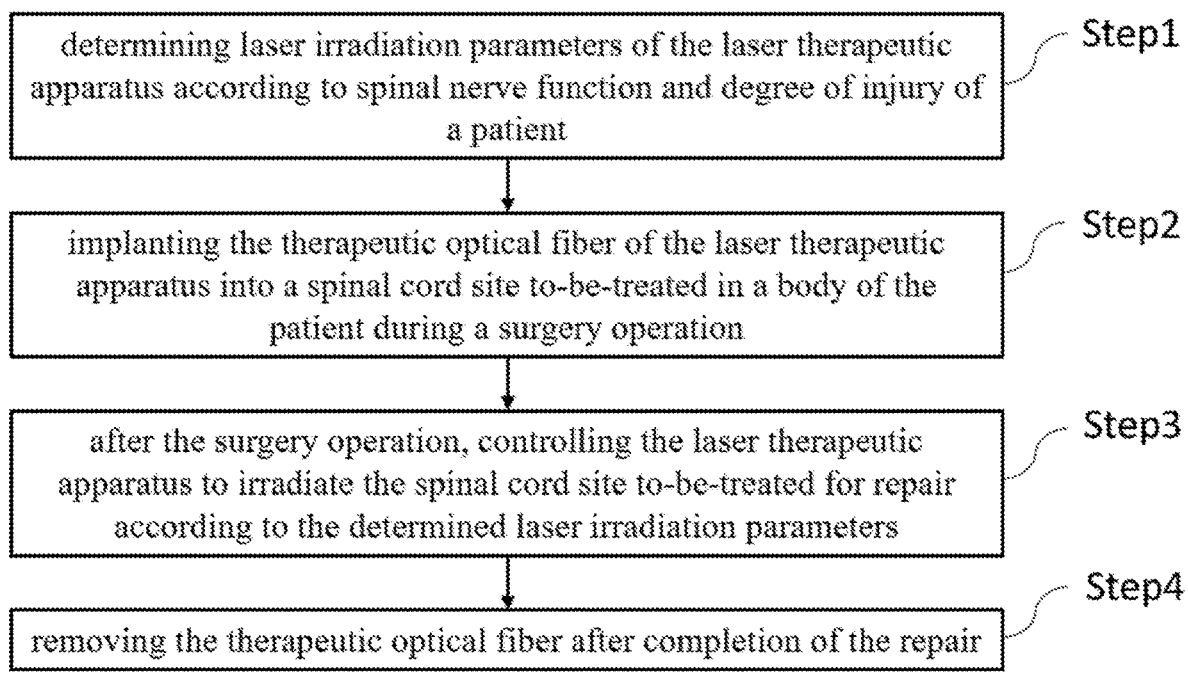
FIG. 7 is a flowchart of a spinal cord repairing method according to an embodiment of the disclosure.

Referring to FIG. 7, FIG. 7 is a flowchart of a spinal cord repairing method according to an embodiment of the disclosure. The repairing method can include the following steps 1 through 4.

Step 1, determining laser irradiation parameters of a laser therapeutic apparatus according to spinal nerve function and degree of injury of a patient;

Step 2, implanting a therapeutic optical fiber of the laser therapeutic apparatus into a spinal cord site to-be-treated in a body of the patient during a surgery operation;

Step 3, after the surgery operation, controlling the laser therapeutic apparatus to irradiate the spinal cord site to-be-treated for repair according to the determined laser irradiation parameters;

Step 4, removing the therapeutic optical fiber after completion of the repair.

Specifically, the laser irradiation parameters include laser working mode, laser wavelength, laser irradiation intensity, and laser irradiation duration.

Optionally, the repairing method further includes:

Step x, adjusting the laser irradiation parameters according to observed changes in TNF-α factor, IL-6 factor, IL-10 factor, NG2 protein and GAP43 protein of the patient to, so as to make TNF-α factor, IL-6 factor, IL-10 factor, NG2 protein and GAP43 protein reach normal levels within a certain period of time and thereby repair the damaged spinal cord site. The step x can be set before the step 4.

It is noted that, cellular and molecular mechanisms of low-intensity laser therapy are that: mitochondria are considered to be major photoreceptors, which can increase adenosine triphosphate, stimulate oxygen activity, promote calcium influx, and release nitric oxide. Subsequent activation of the transcription factor initiates multiple protection, anti-apoptotic, anti-oxidant and pro-proliferative gene product expression.

Specifically, in combination with the laser therapeutic apparatus, the repairing method is specifically that:

1. after a spinal decompression surgery, the surgical operator places the therapeutic optical fiber into a spinal decompression window through the patient's skin under direct vision, makes a light-emitting segment of the therapeutic optical fiber be matched with the position of the decompression window, and leave the other end of the therapeutic optical fiber outside the patient's skin as a laser end;

2. returning to the ward after the surgery operation, the medical operator connects the laser end of the therapeutic optical fiber or the therapeutic optical fiber interface exposed to the skin to a dedicated laser according to factors such as the patient's condition and surgical procedure, and sets up several indexes of the laser such as emission power, irradiation mode, irradiation waveband and irradiation time; a laser light emitted by the laser is guided into the wound through the therapeutic optical fiber to directly irradiate the spinal decompression site and the spinal nerve at a close distance, and thereby achieving repair and therapeutic effect.

3. As per the above-mentioned manner, carries out a intermittent or continuous irradiation after the surgery operation with a period of 7-21 days, the laser treatment is stopped according to the therapeutic effect, the optical fiber is pulled out through the skin penetration site, the surgical suture closes the lumen, and the whole process of treatment ends.

In this embodiment, the spinal cord is repaired and the therapeutic effect is enhanced by implanting the therapeutic optical fiber into the wound of the human body in combination with postoperative intermittent or continuous laser irradiation.

Embodiment 4

With reference to the contents of the Embodiment 1 through the Embodiment 3, this embodiment specifically describes how to implement the treatment by parameter setting in different application scenarios. For details, refer to the following application scenarios.

Application scenario 1: taking the treatment of lumbar vertebrae 4-5 intervertebral disc herniation as an example, after surgical resection of the half or all of the lumbar 4 lamina decompression, an effective irradiation site of the therapeutic optical fiber is located on unilateral or bilateral residual lamina of the lumbar 4 and caudal side of articular process, and lamina of the lumbar 5 and cephalic side of articular process. Laser irradiation parameters were selected as that: irradiation wavelength 808 nm, irradiation energy 500 mW, continuous irradiation for 2 hours per day from 1st to 3rd day after surgery, pulsed irradiation for 2 hours per day from 4th to 30th day after the surgery. The pulsed irradiation scheme is that stops for 0.2 seconds per 1 second of irradiation.

Application Scenario 2: all intervertebral disc protrusions from the first vertebral body of cervical vertebrae to the sacral vertebrae can be treated according to a similar scheme of the application scenario 1, and from one intervertebral space protrusion to a plurality of intervertebral disc protrusions can be treated according to the scheme in the application scenario 1. Laser irradiation parameters are that: irradiation wavelength 800-820 nm, irradiation energy 300-500 mW, continuous irradiation for 1-2 hours per day from 1st to 3rd day after surgery, and pulsed irradiation for 2-3 hours per day from 4th to 30th day after the surgery. The pulsed irradiation scheme is that stops for 0.2-2 seconds per 1-3 seconds of irradiation.

Application scenario 3: taking the treatment of lumbar vertebrae 4-5 spinal canal stenosis as an example, after surgical resection of the half or all of the lumbar 4 lamina decompression, an effective irradiation site of the therapeutic optical fiber is located on unilateral or bilateral residual lamina of the lumbar 4 and caudal side of articular process, and lamina of the lumbar 5 and cephalic side of articular process. Laser irradiation parameters were selected as that: irradiation wavelength 780 nm, irradiation energy 400 mW, continuous irradiation for 1 hour per day from 1st to 4th day after surgery, pulsed irradiation for 1 hour per day from 5th to 30th day after the surgery. The pulsed irradiation scheme is that stops for 1 second per 2 seconds of irradiation.

Application scenario 4: all spinal stenosis from the first vertebral body of the cervical vertebrae to the sacral vertebrae can be treated as per a similar manner as that in the application Scenario 3, and from one segmental spinal stenosis to multiple segmental spinal stenosis can be treated according to the scheme in the application scenario 3. Laser irradiation parameters are that: irradiation wavelength 780-800 nm, irradiation energy 200-400 mW, continuous irradiation for 1-2 hours per day from 1st to 4th day after surgery, and pulsed irradiation for 2-3 hours per day from 5th to 30th day after the surgery. The pulsed irradiation scheme is that stops for 0.2-2 seconds per 1-3 seconds of irradiation.

Application scenario 5: taking the treatment of lumbar vertebrae 4 spondylolisthesis as an example, after surgical resection of the half or all of the lumbar 4 lamina decompression, an effective irradiation site of the therapeutic optical fiber is located on the unilateral or bilateral residual lamina of the lumbar 4 and caudal side of articular process, and lamina of the lumbar 5 and cephalic side of articular process. Laser irradiation parameters are that: irradiation wavelength 770 nm, irradiation energy 200 mW, continuous irradiation for 1 hour per day from 0th to 1st day after surgery, pulsed irradiation for 2-3 hours per day from 2nd to 30th day after the surgery. The pulsed irradiation scheme is that stops for 0.2-2 seconds per 3-5 seconds of irradiation.

Application Scenario 6: all vertebral body spondylolisthesis from the first vertebral body of cervical vertebrae to the sacral vertebrae can be treated according to a similar scheme of the application scenario 5. From one vertebral spondylolisthesis to continuous or intermittent multiple vertebral body spondylolisthesis can be treated according to the scheme in the application scenario 5. Laser irradiation parameters are that: irradiation wavelength 760-780 nm, irradiation energy 100-300 mW, continuous irradiation for 0-1 hour per day from 0th to 1st day after surgery, and pulsed irradiation for 2-3 hours from 2nd to 30th day after the surgery. The pulsed irradiation scheme is that stops for 0.2-2 seconds per 1-3 seconds of irradiation.

Application scenario 7: taking the treatment of lumbar vertebrae lumbar 4 unilateral or bilateral isthmus as an example, after surgical resection of the half or all of the lumbar 4 lamina decompression, an effective irradiation site of the therapeutic optical fiber is located on the unilateral or bilateral residual lamina of the lumbar 4 and caudal side of articular process, and lamina of the lumbar 5 and cephalic side of articular process. Laser irradiation parameters were selected as that: irradiation wavelength 815 nm, irradiation energy 600 mW, continuous irradiation for 3 hours per day from 0th to 6th day after surgery, and continuous irradiation for 1 hour per day from 7th to 30th day after the surgery.

Application scenario 8: unilateral or bilateral isthmic fissures from the lamina of the lumbar 1 to the lamina of the lumbar 5 can be treated according to a similar scheme of the application scenario 7, and consecutive or intermittent multiple unilateral or bilateral isthmic fissures can be treated according to the scheme in the application scenario 7. Laser irradiation parameters are that: irradiation wavelength 800-820 nm, irradiation energy 500-700 mW, continuous irradiation for 2.5-3.5 hours per day from 0th to 6th day after surgery, and continuous irradiation for 0.5-1.5 hours daily from 7th to 30th day after the surgery.

Application scenario 9: taking unilateral or bilateral ligamentum flavum ossification of lumbar vertebrae lumbar 4 as an example, after surgical resection of the half or all of the lumbar 4 lamina decompression, an effective irradiation site of the therapeutic optical fiber is located on the unilateral or bilateral residual lamina of the lumbar 4 and caudal side of articular process, and lamina of the lumbar 5 and cephalic side of articular process. Laser irradiation parameters are that: irradiation wavelength 825 nm, irradiation energy 700 mW, continuous irradiation for 4 hours per day from 0th to 7th day after surgery, and pulsed irradiation for 2-3 hours per day from 8th to 30th days after the surgery. The pulsed irradiation scheme is that stops for 1-2 seconds per 5-8 seconds of irradiation.

Application scenario 10: the unilateral or bilateral ligamentum flavum ossification from the first vertebral body of cervical vertebrae to the tibial lamina can be treated according to a similar scheme of the application scenario 9. The continuous or intermittent multiple unilateral or bilateral ligamentum ligament ossification can be treated according to the scheme in the application scenario 9. Laser irradiation parameters: irradiation wavelength 810-830 nm, irradiation energy 600-800 mW, continuous irradiation for 3.5-4.5 hours per day from 0th to 7th day after the surgery, and pulsed irradiation for 2-3 hours from 8th to 30th day after the surgery. The pulsed irradiation scheme is that stops for 1 to 2 seconds per 5 to 8 seconds of irradiation.

Application scenario 11: taking the treatment of lumbar vertebrae lumbar vertebrae, lamina or facet joint fracture as an example, after surgical resection of the half or all of the lumbar 4 lamina decompression, an effective irradiation site of the therapeutic optical fiber is located on unilateral or bilateral residual lamina of the number 4 and caudal side of articular process, and lamina of the lumbar 5 and cephalic side of articular process. Laser irradiation parameters were selected as that: irradiation wavelength 835 nm, irradiation energy 800 mW, daily pulsed irradiation for 5 hours from 0th to 8th day after surgery which the pulsed irradiation scheme is that stops for 3 seconds per 9 seconds of irradiation, and continuous irradiation for 4 hours per day from 9th to 30th day after surgery.

Application Scenario 12: various types of vertebral bodies, lamina and facet joint fractures from the position of the occipital foramen, the first vertebral body of cervical vertebrae to the tibial lamina can be treated according to a similar scheme of the application scenario 11. Multiple segmental vertebral, lamina, and facet fractures can be treated in a continuous or intermittent manner according to the scheme of Application 11. Laser irradiation parameters: irradiation wavelength 825 to 845 nm, irradiation energy 700-900 mW, pulsed irradiation for 4 to 6 hours per day from 0th to 8th day after the surgery which the pulsed irradiation scheme is that stops for 2 to 3 seconds per 8 to 10 seconds of irradiation, and daily continuous irradiation for 3.5 to 4.5 hours from 9th to 30th day after the surgery.

Application scenario 13: taking the treatment of primary tumors and metastases at any position in the spinal canal 4 vertebral body as an example, after surgical removal of the tumor and removal of half or all of the lumbar 4 lamina decompression, an effective irradiation site of the therapeutic optical fiber is located on the unilateral or bilateral residual lamina of the lumbar 4 and the facet, and the side of the lamina of the lumbar 5 and the facet. Laser irradiation parameters were selected as that: irradiation wavelength 855 nm, irradiation energy 800 mW, continuous irradiation for 6 hours per day from 0th to 9th day after the surgery, and continuous irradiation for 6 hours per day from 10th to 30th day after the surgery.

Application Scenario 14: primary tumors and metastases can be treated from the first vertebral body of cervical vertebrae to the sacral canal at any position according to a similar scheme of the application scenario 13. Primary or metastatic tumors at any location within the spinal canal can be treated continuously or intermittently according to the scheme of Application 13. Laser irradiation parameters: irradiation wavelength 840-870 nm, irradiation energy 700-900 mW, continuous irradiation for 5 to 7 hours per day from 0th to 9th day after the surgery, and continuous irradiation for 5 to 7 hours daily from 10th to 30th day after the surgery.

Application scenario 15: taking the treatment of hemorrhage and hematoma at any position in the spinal canal 4 vertebral body as an example, relieve bleeding and hematoma occupying pressure during surgery, and remove half or all of the lumbar 4 lamina decompression, an effective irradiation site of the therapeutic optical fiber is located on the unilateral or bilateral residual lamina of the lumbar 4 and the facet, and the side of the lamina of the lumbar 5 and the facet. Laser irradiation parameters were selected as that: irradiation wavelength 750 nm, irradiation energy 200 mW, pulsed irradiation for 5 hours per day from 0th to 10th day after the surgery which the pulsed irradiation scheme is that stops for 3 seconds per 12 seconds of irradiation, and continuous irradiation for 4 hours per day for 11th to 30th day after the surgery.

Application Scenario 16: the hemorrhage and hematoma can be treated from the first vertebral body of cervical vertebrae to the sacral canal at any position according to a similar scheme of the application scenario 15. The continuous or intermittent multiple hemorrhage and hematoma in the spinal canal can be treated according to the scheme in the application scenario 15. Laser irradiation parameters: irradiation wavelength 730-770 nm, irradiation energy 100-300 mW, pulsed irradiation for 4 to 6 hours per day from 0th to 10th day after the surgery which the pulsed irradiation scheme is that stops for 4 to 5 seconds per 10 to 14 seconds of irradiation, and continuous irradiation for 3 to 5 hours daily for 11th to 30th day after the surgery.

Application scenario 17: taking sagittal or coronal position of the lumbar vertebral body and the sagittal coronal curvature as an example, after orthopedic surgery to correct the sagittal coronal scoliosis, resection of the hemi- or all lumbar 4 lamina decompression, an effective irradiation site of the therapeutic optical fiber is located on the unilateral or bilateral residual lamina of the lumbar 4 and the facet, and the side of the lamina of the lumbar 5 and the facet. Laser irradiation parameters were selected as that: irradiation wavelength 720 nm, irradiation energy 900 mW, continuous irradiation for 4 hours per day from 0th to 10th day after the surgery, and continuous irradiation for 4 hours daily from 11th to 30th day after the surgery.

Application Scenario 18: the sagittal or coronal position of the cervical vertebrae to the sagittal vertebral body and the simultaneous sagittal coronal scoliosis can be treated according to a similar scheme of the application scenario 17. Continuous or intermittent multiple sagittal or coronal vertebral bodies and simultaneous sagittal coronal scoliosis can be treated according to the scheme of Application 17. Laser irradiation parameters are selected as that: irradiation wavelength 700-740 nm, irradiation energy 800-1000 mW, continuous irradiation for 3 to 5 hours per day from 0th to 9th day after the surgery, and continuous irradiation for 3 to 5 hours daily from 10th to 30th day after the surgery.

Application scenario 19: taking the treatment of a flat lumbar 4 vertebral canal infection as an example, after removing the wound and the contaminant during the operation, the half or all of the lumbar 4 lamina decompression is removed. An effective irradiation site of the therapeutic optical fiber is located on the unilateral or bilateral residual lamina of the lumbar 4 and the facet, and the side of the lamina of the lumbar 5 and the facet. Laser irradiation parameters were selected as that: irradiation wavelength 700 nm, irradiation energy 700 mW, continuous irradiation for 3 hours per day from 0th to 12th day after the surgery, 13th to 30th day after the surgery, pulsed irradiation for 6 hours. The pulsed irradiation scheme is that stops for 2 seconds per 20 seconds of irradiation.

Application scenario 20: the intraspinal infection from the first vertebral body of cervical vertebrae to the humerus can be treated in a similar manner to the application scenario 19. After the wounds and contaminants are removed during the procedure, multiple consecutive or intermittent intraspinal infections can be treated according to the scheme of Application 19. Laser irradiation parameters: irradiation wavelength 680-710 nm, irradiation energy 200-400 mW, daily continuous irradiation for 2 to 4 hours from 0th to 12th day after the surgery, pulsed irradiation for 5 to 7 hours per day from 13th to 30th day after the surgery. The pulsed irradiation scheme is that stops for 3 to 5 seconds per 10 to 30 seconds of irradiation.

Application scenario 21: taking the treatment of lumbar vertebrae 4-5 disc discogenic low back pain and other pain sources of lumbar vertebrae 4-5 section low back pain as an example, after surgical resection of the half or all of the lumbar 4 lamina decompression, an effective irradiation site of the therapeutic optical fiber is located on the unilateral or bilateral residual lamina of the lumbar 4 and coronal caudal side of articular process, and lamina of the lumbar 5 and cephalic side of articular process. Laser irradiation parameters were selected as that: irradiation wavelength 750 nm, irradiation energy 600 mW, continuous irradiation for 1 hour per day from 1st to 5th day after the surgery, pulsed irradiation for 4 hours per day from 6th to 30th day after the surgery. The pulsed irradiation scheme is that stops for 3 seconds per 3 seconds of irradiation.

Application scenario 22: all of the disc-derived low back pain from the first vertebral body of cervical vertebrae to the sacral vertebrae can be treated in a similar manner as in the application scenario 21, as well as other pain sources of low back pain. The pain from one site to the entire spine can be treated according to the scenario 21 scenario. Laser irradiation parameters: irradiation wavelength 730-770 nm, irradiation energy 500-700 mW, continuous irradiation for 0.5 to 2 hours per day from 1st to 5th day after the surgery, and pulsed irradiation for 3 to 5 hours per day from 6th to 30th day after the surgery. The pulsed irradiation scheme is that stops for 1 to 2 seconds per 20 to 30 seconds of irradiation.

Application Scene 23: taking the treatment of low back pain in the lower back as an example, an effective irradiation site of the therapeutic optical fiber is placed on the skin surface, subcutaneous, superficial fascia, deep fascia and muscle layer by surgical incision or percutaneous puncture. Laser irradiation parameters were selected as that: irradiation wavelength 900 nm, irradiation energy 900 mW, continuous exposure for 2 hours per day from 1st to 8th day after the surgery, followed by pulsed irradiation for 3 hours per day from 9th to 30th day. The pulsed irradiation scheme is that stops for 10 seconds per 60 seconds of irradiation.

Application Scenario 24: acute and chronic pain from the neck, chest, waist, and appendix can be treated in a similar manner as in Application scenario 23. Acute and chronic pain from one site to the entire back can be treated according to the scheme of Application 23. Laser irradiation parameters: irradiation wavelength 880-920 nm, irradiation energy 800-1000 mW, continuous exposure for 2 to 4 hours per day from 1st to 8th day after the surgery, followed by pulsed irradiation for 2 to 4 hours per day from 9th to 30th day after the surgery. The pulsed irradiation scheme is that stops for 10 to 20 seconds per 60 to 120 seconds of irradiation.

In this embodiment, the spinal fiber is repaired and the therapeutic effect is enhanced by implanting the therapeutic optical fiber into the wound of the human body in combination with postoperative intermittent or continuous laser irradiation.

In the several embodiments provided by the disclosure, it should be understood that the disclosed system, apparatus, and method may be implemented in other manners. For example, the device embodiments described above are merely illustrative. For example, the division of the unit is only a logical function division, and the actual implementation may have another division manner. For example, multiple units or components may be combined or integrated into another system, or some features may be omitted or not performed. In addition, the mutual coupling or direct coupling or communication connection shown or discussed may be an indirect coupling or communication connection through some interface, device or unit, and may be in an electrical, mechanical or other form.

The units described as separate components may or may not be physically separated, and the components displayed as units may or may not be physical units, that is, may be located in one place, or may be distributed to multiple network units. Some or all of the units may be selected according to actual needs to achieve the purpose of the solution of the embodiment.

In addition, each functional unit in each embodiment of the disclosure may be integrated into one processing unit, or each unit may exist physically separately, or two or more units may be integrated into one unit. The above integrated unit can be implemented in the form of hardware or in the form of hardware plus software functional units.

The above-described integrated unit implemented in the form of a software functional unit can be stored in a computer readable storage medium. The software functional units described above are stored in a storage medium and include instructions for causing a computer device (which may be a personal computer, server, or network device, etc.) to perform portions of the steps of the methods described in various embodiments of the disclosure. The foregoing storage medium includes various media that can store program codes, such as a USB flash drive, a removable hard disk, a read only memory (ROM), a random access memory (RAM), a magnetic disk, or an optical disk.

Finally, it should be noted that the above embodiments are only used to illustrate the technical solutions of the disclosure, and are not limited thereto; although the disclosure has been described in detail with reference to the foregoing embodiments, those skilled in the art should understand that the technical solutions described in the foregoing embodiments may be modified or equivalently substituted for some of the technical features. The modifications and substitutions of the disclosure do not depart from the spirit and scope of the technical solutions of the embodiments of the disclosure.

What is claimed is:
1. A laser therapeutic apparatus, comprising:
a laser; and
a therapeutic optical fiber, coupled to the laser and driven by the laser to emit light;
wherein the therapeutic optical fiber is configured for being implanted into a human body of a patient during surgery to perform a repair treatment on a spinal cord site to-be-treated by light irradiation in a manner of first continuous irradiation with a first total time length and then pulsed irradiation with a second time length greater than the first total time length or in a manner of first pulsed irradiation with a third total time length and then continuous irradiation with a fourth total time length greater than the third total time length, and then configured for being removed from the human body of the patient after the surgery;
wherein the therapeutic optical fiber comprises N number of laser fibers each with a predetermined length, N−1 number of optical fiber connection components, an optical fiber guiding structure, and an optical fiber controller; the N number of laser fibers are coupled with one another by the N−1 number of optical fiber connection components to form a cascaded optical fiber structure, an end of the cascaded optical fiber structure is coupled to the optical fiber guiding structure, and another end of the cascaded optical fiber structure is coupled to the optical fiber controller, and N is a positive integer no smaller than 2; each of the optical fiber connection components is provided with a pressure sensor, and the pressure sensor is coupled to the optical fiber controller, the pressure sensor is configured to detect pressure data of the optical fiber connection component, and the optical fiber controller is configured to determine whether the N number of laser fibers are displaced in human body tissue and thereby avoid medical accidents based on the pressure data;
wherein each of the N number of laser fibers comprises a core, a cladding layer, a metal coating layer, an elastic coating layer and a hydrophilic layer arranged in that order from inside to outside;
wherein a color of the optical fiber guiding structure is different from that of other parts of the therapeutic optical fiber;
wherein the optical fiber guiding structure is used as a guiding needle for skin penetration;
wherein the optical fiber connection component comprises a first collimator and a second collimator; the first collimator and the second collimator are respectively disposed ends of adjacent two of the N number of laser fibers, and the first collimator and the second collimator are attached to each other such that the adjacent two of the N number of laser fibers are axially coincided with each other;

wherein the optical fiber connection component further comprises a silicone rubber sleeve, the silicone rubber sleeve is sleeved on the first collimator and the second collimator, the pressure sensor is disposed between the silicone rubber sleeve and the first and second collimators and overlapped with the first and second collimators as well as the silicone rubber sleeve;

wherein a lateral limiting ring is further disposed at an interface between the laser fiber and a corresponding one of the first and second collimators;

wherein a distance from the lateral limiting ring to the corresponding one of the first and second collimators is in a range from 2 mm to 8 mm;

wherein a ratio of a diameter of the lateral limiting ring to a diameter of the laser fiber is in a range from 4:3 to 3:2; and wherein the lateral limiting ring is coated with a tetrafluoroethylene coating.

2. The laser therapeutic apparatus according to claim 1, wherein the therapeutic optical fiber is a 360° circumferentially illuminated full-body luminous optical fiber, and the pressure sensor is across an interface between the adjacent two of the N number of laser fibers.

3. A laser therapeutic apparatus, comprising:

a laser; and a therapeutic optical fiber, coupled to the laser and driven by the laser to emit light;

wherein the therapeutic optical fiber is configured for being implanted into a human body of a patient during surgery to perform a repair treatment on a spinal cord site to-be-treated by irradiation and then being removed from the human body of the patient after the surgery;

wherein the therapeutic optical fiber comprises N number of laser fibers each with a predetermined length, N−1 number of optical fiber connection components, an optical fiber guiding structure, and an optical fiber controller; the N number of laser fibers are coupled with one another by the N−1 number of optical fiber connection components to form a cascaded optical fiber structure, an end of the cascaded optical fiber structure is coupled to the optical fiber guiding structure, and another end of the cascaded optical fiber structure is coupled to the optical fiber controller, and N is a positive integer;

wherein the optical fiber connection component comprises a first collimator and a second collimator; the first collimator and the second collimator are respectively disposed ends of adjacent two of the N number of laser fibers, and the first collimator and the second collimator are attached to each other such that the adjacent two of the N number of laser fibers are axially coincided with each other;

wherein each of the optical fiber connection components is provided with a pressure sensor, and the pressure sensor is coupled to the optical fiber controller, the pressure sensor is configured to detect pressure data of the optical fiber connection component, and the optical fiber controller is configured to determine whether the N number of laser fibers are displaced in human body tissue based on the pressure data;

wherein the pressure sensor is overlapped with both the first and second collimators and thereby across an interface between the adjacent two of the N number of laser fibers.

4. The laser therapeutic apparatus according to claim 3, wherein the therapeutic optical fiber is a 360° circumferentially illuminated full-body luminous optical fiber.

5. The laser therapeutic apparatus according to claim 3, wherein the laser is a semiconductor laser having a laser wavelength of 770 nm to 830 nm.

6. The laser therapeutic apparatus according to claim 3, wherein the optical fiber connection component further comprises a silicone rubber sleeve, the silicone rubber sleeve is sleeved on the first collimator and the second collimator, the pressure sensor is overlapped with all of the silicone rubber sleeve, the first collimator and the second collimator.

7. The laser therapeutic apparatus according to claim 3, wherein a lateral limiting ring is further disposed at an interface between the laser fiber and corresponding one of the first and second collimators.

8. The laser therapeutic apparatus according to claim 7, wherein a distance from the lateral limiting ring to the corresponding one of the first and second collimators is in a range from 2 mm to 8 mm, and a ratio of a diameter of the lateral limiting ring to a diameter of the laser fiber is in a range from 4:3 to 3:2.

9. The laser therapeutic apparatus according to claim 7, wherein the lateral limiting ring is coated with a tetrafluoroethylene coating.

10. The laser therapeutic apparatus according to claim 3, wherein the laser comprises a power source, a processor, a laser output circuit, an input control circuit, and a laser light source;

the processor is electrically coupled to the input control circuit and the laser output circuit and configured for controlling the laser output circuit according to a control instruction inputted from the input control circuit;

the laser output circuit is electrically coupled to the laser light source and configured for controlling an irradiation intensity and an irradiation duration of the laser light source;

the power source is electrically coupled to the laser output circuit and configured for providing a driving current to the laser output circuit.

11. The laser therapeutic apparatus according to claim 10, wherein the laser output circuit comprises a power control circuit and a laser driving circuit;

the power control circuit is electrically coupled to the processor, the power source and the laser driving circuit individually, and configured for converting a rated voltage outputted from the power source into a required constant driving current according to the control instruction inputted to the processor, and further configured for outputting the driving current to the laser driving circuit to drive the laser driving circuit to operate;

the laser driving circuit is electrically coupled to the laser light source and configured for controlling the irradiation intensity and the irradiation duration of the laser light source.

12. The laser therapeutic apparatus according to claim 11, wherein the laser further comprises a feedback protection circuit; the feedback protection circuit comprises an overcurrent protection circuit, a power feedback circuit and a temperature feedback circuit;

the overcurrent protection circuit is electrically coupled to the power control circuit and the processor, and configured for detecting a current of the power control circuit and transmitting a current information to the processor;

the power feedback circuit and the temperature feedback circuit each are electrically coupled to both the laser driving circuit and the processor, and configured for detecting a power and a temperature of the laser driving circuit and transmitting a power information and a temperature information to the processor.

13. A spinal cord repairing method for performing spinal cord repair by a laser therapeutic apparatus as claimed in claim 3, the spinal cord repairing method comprising:
   determining laser irradiation parameters of the laser therapeutic apparatus according to spinal nerve function and degree of injury of a patient;
   implanting the therapeutic optical fiber of the laser therapeutic apparatus into a spinal cord site to-be-treated in a human body of the patient during a surgery operation;
   after the surgery operation, controlling the laser therapeutic apparatus to irradiate the spinal cord site to-be-treated for repair according to the determined laser irradiation parameters, wherein the spinal cord site to-be-treated is irradiated in a manner of first continuous irradiation with a first total time length and then pulsed irradiation with a second total time length greater than the first total time length, or in a manner of first pulsed irradiation with a third total time length and then continuous irradiation with a fourth total time length greater than the third total time length; and
   removing the therapeutic optical fiber after completion of the repair.

14. The method according to claim 13, wherein the laser irradiation parameters comprise working mode of laser irradiation, laser wavelength, laser irradiation intensity, and laser irradiation duration.

15. The method according to claim 13, wherein the method further comprises:
   adjusting the laser irradiation parameters according to observed changes in TNF-α factor, IL-6 factor, IL-10 factor, NG2 protein and GAP43 protein of the patient.

16. The laser therapeutic apparatus according to claim 1, wherein the optical fiber guiding structure is a metal guiding needle which is cut off after the optical fiber enters a surgical field.

17. The laser therapeutic apparatus according to claim 3, wherein the optical fiber guiding structure is a metal guiding needle which is cut off after the optical fiber enters a surgical field.

* * * * *